US012565619B2

(12) United States Patent
Akishika et al.

(10) Patent No.: US 12,565,619 B2
(45) Date of Patent: *Mar. 3, 2026

(54) METHOD FOR PREPARING COAL OR CAKING ADDITIVE AND METHOD FOR PRODUCING COKE

(71) Applicant: JFE STEEL CORPORATION, Tokyo (JP)

(72) Inventors: Issui Akishika, Tokyo (JP); Yusuke Dohi, Tokyo (JP); Daisuke Igawa, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 289 days.

This patent is subject to a terminal disclaimer.

(21) Appl. No.: 18/020,461

(22) PCT Filed: Aug. 5, 2021

(86) PCT No.: PCT/JP2021/029201
§ 371 (c)(1),
(2) Date: Feb. 9, 2023

(87) PCT Pub. No.: WO2022/039044
PCT Pub. Date: Feb. 24, 2022

(65) Prior Publication Data
US 2023/0323211 A1    Oct. 12, 2023

(30) Foreign Application Priority Data
Aug. 17, 2020    (JP) ................................. 2020-137311

(51) Int. Cl.
*C10B 57/08*        (2006.01)
*C10B 47/04*        (2006.01)
(Continued)

(52) U.S. Cl.
CPC .............. *C10B 57/08* (2013.01); *C10B 57/04* (2013.01); *C10B 57/06* (2013.01); *G01N 11/14* (2013.01); *G01N 33/222* (2013.01)

(58) Field of Classification Search
CPC ......... C10B 53/02; C10B 57/04; C10B 57/06; C10B 57/08
See application file for complete search history.

(56) References Cited

U.S. PATENT DOCUMENTS 5,525,196 A        6/1996   Yuda et al.
12,061,140 B2 *    8/2024   Akishika ................. C10B 57/04
(Continued)

FOREIGN PATENT DOCUMENTS

CN        104145181 A   *  11/2014   ............. C10B 57/04
EP        3 263 674 A1      1/2018
(Continued)

OTHER PUBLICATIONS

Espacenent translation of CN-104145181-A.*
(Continued)

*Primary Examiner* — Jonathan Luke Pilcher
(74) *Attorney, Agent, or Firm* — Oliff PLC

(57)        ABSTRACT

A method for preparing a coal, which is used alone or in combination with at least one other coal, or a caking additive as a raw material for coke production. The method includes, before the coal or caking additive is delivered to a coke plant, adjusting a grain size such that the amount of grains with a grain size of 6 mm or more in the coal or caking additive satisfies at least one of a degree of entanglement $(a–b)/a$ of 0.20 or more and a portion having a height a of 30 mm or more is 30% or less by mass. The height a is a height of semicoke adhering to a stirrer, the semicoke formed by heating the coal or caking additive in a container (Continued)

while rotating the stirrer, and the height b is a height of the semicoke on an inner wall of the container.

10 Claims, 3 Drawing Sheets

(51) Int. Cl.
| | | |
|---|---|---|
| *C10B 57/04* | (2006.01) | |
| *C10B 57/06* | (2006.01) | |
| *G01N 11/14* | (2006.01) | |
| *G01N 33/22* | (2006.01) | |

(56) References Cited

U.S. PATENT DOCUMENTS

| | | |
|---|---|---|
| 2015/0007493 A1 | 1/2015 | Dohi et al. |
| 2017/0137716 A1 | 5/2017 | Dohi et al. |
| 2023/0296486 A1* | 9/2023 | Akishika ................. G01N 3/54 |
| | | 702/50 |

FOREIGN PATENT DOCUMENTS

| | | |
|---|---|---|
| JP | H07-145380 A | 6/1995 |
| JP | 2000-304674 A | 11/2000 |
| JP | 2001-323281 A | 11/2001 |
| JP | 2002-129168 A | 5/2002 |
| JP | 2010190761 A | 9/2010 |
| JP | 2012-72388 A | 4/2012 |
| JP | 2014-218647 A | 11/2014 |
| JP | 6565642 B2 | 8/2019 |
| RU | 2 675 567 C1 | 12/2018 |
| WO | 2013/128866 A1 | 9/2013 |
| WO | 2020/189294 A1 | 9/2020 |

OTHER PUBLICATIONS

Hidetosi Morotomi, Nobuo Suzuki, Takasi Miyazu, Masaru Simura, Studies on Test for Plastic Properties of Coal by Gieseler Plastometer, Journal of the Fuel Society of Japan, 1974, vol. 53, Issue 9, pp. 779-790, https://doi.org/10.3775/jie.53.9_779.*

Partial English Translation of Morotomi et al. "Studies on Test for Plastic Properties of Coal by Gieseler Plastometer, Journal of the Fuel Society of Japan" obtained from U.S. Appl. No. 17/439,741.*

Oct. 19, 2021 International Search Report issued in International Patent Application No. PCT/JP2021/029201.

Nov. 22, 2023 Office Action issued in Australian Patent Application No. 2021326589.

Dec. 25, 2024 Office Action issued in Chinese Patent Application No. 202180055860.3 (with concise statement of relevance in English).

Wang Lihua, Wang Wenliang, "Preliminary study on the constant moment Kiel fluidity test method." Clean Coal Technology. vol. 9, No. 4. Dec. 25, 2003. pp. 53-56.

Zhang Dongbo, An Zhanlai, "A brief discussion on the typical curve and influencing factors of bituminous coal colloid layer index." Hebei Enterprises. No. 1. Jan. 10, 2020. pp. 159-160.

Apr. 6, 2022 Office Action issued in Taiwanese Patent Application No. 110129871.

May 23, 2023 Office Action issued in Japanese Patent Application No. 2021-576656.

Aug. 16, 2023 Office Action issued in Russian Patent Application No. 2023102866.

Oct. 31, 2023 Office Action issued in U.S. Appl. No. 17/439,741.

Mar. 20, 2024 Office Action issued in U.S. Appl. No. 17/439,741.

May 16, 2025 Office Action issued in U.S. Appl. No. 18/020,555.

* cited by examiner (a)                                (b)

(a)                                (b)

(a)          (b)

◇ BLENDING RATIO OF COAL RATED
   AS POOR ≤ 2% BY MASS

● 8% BY MASS ≤ BLENDING RATIO
   OF COAL RATED AS POOR ≤ 12% BY MASS

BLENDING RATIO OF COAL WITH GRAIN SIZE OF 6 mm OR MORE (% BY MASS)

METHOD FOR PREPARING COAL OR CAKING ADDITIVE AND METHOD FOR PRODUCING COKE

TECHNICAL FIELD

This application relates to a preparation method for adjusting the grain size of a coal or a caking additive, that is, a method for producing a coal or a caking additive with an adjusted grain size, in order that high-strength coke can be produced by using an evaluation method for evaluating the thermoplasticity of a coal or a caking additive.

BACKGROUND

Metallurgical coke used as a blast furnace raw material to produce pig iron in a blast furnace preferably has high strength. Low-strength coke degrades in a blast furnace, reduces the gas permeability in the blast furnace, and cannot stably produce pig iron. Thus, to produce high-strength coke, there is a need for a technique for examining coal as a raw material for metallurgical coke from the perspective of not reducing coke strength.

Patent Literature 1 discloses that coal in a plastic state has a major effect on the quality of coke in a coking process in a coke oven. Thus, in the examination of coal, it is important to accurately evaluate the properties of the plastic state of coal. As described in Patent Literature 1, the measurement of fluidity by a Gieseler plastometer method specified in JIS-M8801 is known as an evaluation method.

CITATION LIST

Patent Literature

PTL 1: Japanese Unexamined Patent Application Publication No. 2000-304674

Non Patent Literature

NPL 1: MIYAZU Takashi et al., "Tashu haigo keikaku narabini genryotan no hyoka (The Blending Design Using Many Kinds of Coal and the Evaluation System for Single Coal)", Nippon Kokan Technical Report, vol. 67, 1975, pp. 125-137

SUMMARY

Technical Problem

It is known that fluidity measured by the Gieseler plastometer method cannot simulate a phenomenon in an actual coke oven. Thus, there is a problem that estimation of the quality of coke using as an index the fluidity of coal measured by the Gieseler plastometer method is inadequate in terms of accuracy. Thus, there is a need for a technique for producing metallurgical coke using an index other than the fluidity of coal. In view of the related art, it is an object of the disclosed embodiments to provide a method for preparing a coal or a caking additive by evaluating the possibility of a target coal reducing coke strength and by adjusting the grain size of a coal that can reduce coke strength.

Solution to Problem

Means for solving these problems are described below.

[1] A method for preparing a coal, which is used alone or in combination with another coal or other coals, or a caking additive as a raw material for coke production, including: before the coal or caking additive is delivered to a coke plant, adjusting a grain size such that the amount of grains with a grain size of 6 mm or more in the coal or caking additive satisfying at least one of a degree of entanglement, $(a-b)/a$, of 0.20 or more and a height, a, of 30 mm or more is 30% or less by mass, wherein a denotes a height of semicoke adhering to a stirrer, the semicoke being formed by heating the coal or caking additive in a container while rotating the stirrer, and b denotes a height of the semicoke on an inner wall of the container.

[2] A method for preparing a coal, which is used alone or in combination with another coal or other coals, or a caking additive as a raw material for coke production, including: before the coal or caking additive is delivered to a coke plant, adjusting a grain size such that the amount of grains with a grain size of 6 mm or more in the coal or caking additive satisfying at least one of a degree of entanglement, $(a-b)/a$, of 0.20 or more and a height, a, of 30 mm or more satisfies the following formula (1), wherein a denotes a height of semicoke adhering to a stirrer, the semicoke being formed by heating the coal or caking additive in a container while rotating the stirrer, and b denotes a height of the semicoke on an inner wall of the container, $$\text{amount of grains with a grain size of 6 mm or more} \atop (\% \text{ by mass}) \leq 30 + 0.5 \times (\text{HGI} - 60) \qquad (1)$$

wherein HGI denotes a Hardgrove grindability index of the coal or caking additive.

[3] The method for preparing a coal or a caking additive according to [1] or [2], wherein conditions for rotating the stirrer while heating the container and the coal or caking additive in the container are measurement conditions for Gieseler fluidity.

[4] A method for preparing a coal, which is used alone or in combination with another coal or other coals, or a caking additive as a raw material for coke production, including: before the coal or caking additive is delivered to a coke plant, for a plurality of coals or caking additives, determining in advance the range of a degree of entanglement, $(a-b)/a$, or a height, a, rated as poor as the raw material for coke production on the basis of the relationship between the degree of entanglement, $(a-b)/a$, or the height, a, and the strength of coke produced by mixing the plurality of coals or caking additives with another coal or other coals and by carbonization, wherein a denotes a height of semicoke adhering to a stirrer, the semicoke being formed by heating the plurality of coals or caking additive in a container while rotating the stirrer, and b denotes a height of the semicoke on an inner wall of the container; and adjusting a grain size of the coal or caking additive used as the raw material for coke production such that the amount of grains with a grain size of 6 mm or more in the coal or caking additive with the degree of entanglement, $(a-b)/a$, or the height, a, rated as poor as the raw material for coke production is 30% or less by mass.

[5] A method for preparing a coal, which is used alone or in combination with another coal or other coals, or a caking additive as a raw material for coke production, including: before the coal or caking additive is delivered to a coke plant, for a plurality of coals or caking additives, determining in advance the range of a degree of entanglement, $(a-b)/a$, or a height, a, rated as poor as the raw material for coke production on the basis of the relationship between the degree of entanglement, $(a-b)/a$, or the height, a, and the strength of coke produced by mixing the plurality of coals or caking additives with another coal or other coals and by carbonization, wherein a denotes a height of semicoke adhering to a stirrer, the semicoke being formed by heating the plurality of coals or caking additive in a container while rotating the stirrer, and b denotes a height of the semicoke on an inner wall of the container; and adjusting a grain size of the coal or caking additive used as the raw material for coke production such that the amount of grains with a grain size of 6 mm or more in the coal or caking additive with the degree of entanglement, (a−b)/a, or the height, a, rated as poor as the raw material for coke production satisfies the following formula (1):

$$\text{amount of grains with a grain size of 6 mm or more} \atop (\% \text{ by mass}) \leq 30 + 0.5 \times (\text{HGI}-60) \tag{1}$$

wherein HGI denotes a Hardgrove grindability index of the coal or caking additive.

[6] The method for preparing a coal or a caking additive according to any one of [1] to [5], including: before the coal or caking additive is charged into the coke oven, adjusting the grain size such that the amount of grains with a grain size of 6 mm or more in the coal or caking additive is 5% or less by mass.

[7] The method for preparing a coal or a caking additive according to any one of [1] to [6], including: before the coal or caking additive is delivered from a place where the coal or caking additive is produced, adjusting the grain size of the coal or caking additive.

[8] A method for producing coke, including: carbonizing a coal prepared by the method for preparing a coal or a caking additive according to any one of [1] to [7].

[9] A method for producing coke, including: carbonizing a coal and a caking additive prepared by the method for preparing a coal or a caking additive according to any one of [1] to [7].

Advantageous Effects

The disclosed embodiments include determining whether the coal is defective coal that can reduce coke strength and adjusting the grain size of a coal rated as poor. This can reduce the decrease in the coke strength of coke produced even using a coal that can reduce the coke strength, and allows high-strength metallurgical coke to be produced.

DESCRIPTION OF EMBODIMENTS

In the disclosed embodiments, whether the coal corresponds to a coal whose strength can be reduced is determined using as an index the shape of semicoke formed by heating the coal in an apparatus that includes a container for the coal and a stirrer located in the container. The disclosed embodiments have been completed by finding that the decrease in the coke strength of produced coke can be reduced by adjusting in advance the grain size of a coal that is determined to possibly reduce the coke strength and using the coal alone or in combination with another coal as a raw material for coke production. The disclosed embodiments are further described below.

Figure 1:
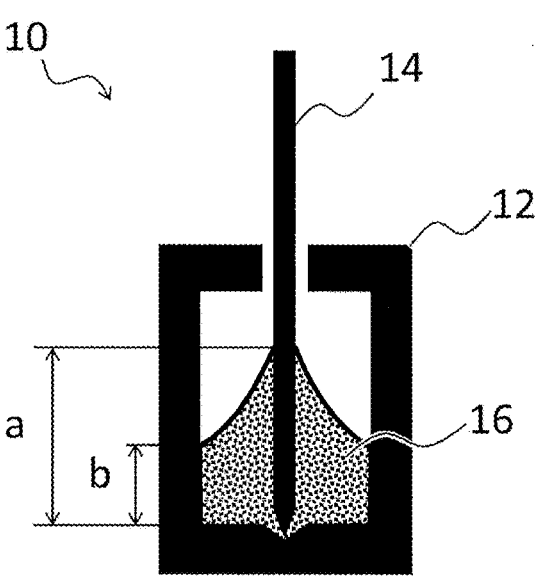
FIG. 1 is a vertical cross-sectional view of an example of a Gieseler plastometer 10 used in a method for evaluating the thermoplasticity of a coal according to the present embodiment.

FIG. 1 is a vertical cross-sectional view of an example of a Gieseler plastometer 10 used in a method for evaluating the thermoplasticity of a coal according to the present embodiment. The Gieseler plastometer 10 includes a container 12 for a coal to be examined and a stirrer 14 located in the container 12. The Gieseler plastometer 10 further includes a drive unit (not shown), which rotates the stirrer 14. When the container 12 containing coal is heated while the stirrer 14 is rotated, the heated coal has a thermoplastic state. The coal in the thermoplastic state deforms as a viscoelastic body and becomes entangled with the rotating stirrer 14. Force to maintain the shape acts on the coal, and force to resist the rotation acts on the stirrer 14.

In a Gieseler plastometer method, the rotational speed of the stirrer 14 is measured while a predetermined torque is applied to the stirrer 14, and the maximum rotational speed during heating is determined as a Gieseler maximum fluidity MF (ddpm). The measured value may be represented by the common logarithm log of the Gieseler maximum fluidity expressed in log MF. The coal heating conditions and the conditions for measuring the dimensions of the container 12 or the like in the Gieseler plastometer method are specified in JIS M 8801 as described below.

(1) A stirrer having a shaft with a diameter of 4.0 mm and four horizontal bars (1.6 mm in diameter, 6.4 mm in length, not shown in FIG. 1) perpendicular to the shaft is placed in a container with a depth of 35.0 mm and an inner diameter of 21.4 mm.

(2) The container is filled with 5 g of coal.

(3) The container is immersed in a metal bath preheated to 300° C. or 350° C. After the temperature of the metal bath returns to the preheating temperature, heating at a rate of 3° C./min is continued until the rotation of the stirrer stops.

The distance between the lowest horizontal bar and the bottom of the container is 1.6 mm, and the distance between the horizontal bars in the axial direction is 3.2 mm. The two central horizontal bars form an angle of 180 degrees in the rotational direction. The upper and lower horizontal bars also form an angle of 180 degrees in the rotational direction. The two central horizontal bars and the two upper and lower horizontal bars form an angle of 90 degrees in the rotational direction. The conditions specified in ASTM D2639 are also similar to those in JIS M 8801, and the ASTM method may be used. ISO 10329 and its corresponding conditions may also be used. When the Gieseler plastometer is not used, the coal container preferably has a cylindrical shape, and the stirrer preferably has a diameter corresponding to 5% to 60% of the inner diameter of the container. Although the stirrer preferably has a horizontal bar, molten coal becomes entangled with the stirrer even without the horizontal bar.

Upon heating, coal is thermally plasticized, and flows. Further heating re-solidifies the plasticized coal. Thus, after the Gieseler fluidity is measured, coal heated at a temperature equal to or higher than the re-solidification temperature of the coal becomes semicoke 16 and is contained in the container 12. The coal and the semicoke 16 are also plastic.

carbonization test, an electric furnace that can simulate the carbonization conditions of a coke oven was used, and a coal blend charged in the furnace at a bulk density of coal charge of 750 kg/dry coal was carbonized at 1050° C. for 6 hours to produce coke. Table 1 shows the properties, the degree of entanglement, $(a-b)/a$, and the height, a, of the prepared coals.

TABLE 1

| Item | Ash [%] | Volatile matter [%] | Ro [%] | TI [%] | log MF [log ddpm] | Height a [mm] | Height b [mm] | Degree of entanglement |
|------|---------|---------------------|--------|--------|-------------------|---------------|---------------|------------------------|
| Coal T | 7.8 | 35.7 | 0.87 | 14.6 | 4.19 | 33.4 | 17.3 | 0.48 |
| Coal U | 6.2 | 30.6 | 1.07 | 11.5 | 3.12 | 30.8 | 19.0 | 0.38 |
| Coal V | 6.8 | 42.1 | 0.62 | 20.2 | 4.35 | 29.4 | 26.0 | 0.12 |
| Coal W | 8.6 | 32.0 | 1.03 | 35.5 | 3.05 | 25.9 | 24.4 | 0.06 |
| Coal X | 8.1 | 34.1 | 0.95 | 29.0 | 2.70 | 27.0 | 25.1 | 0.07 |
| Coal Y | 7.3 | 33.8 | 0.93 | 33.9 | 2.49 | 26.0 | 21.6 | 0.17 |

After the measurement of the Gieseler fluidity, therefore, the semicoke 16 comes into contact with the inner wall of the container 12 but is pulled by the stirrer 14 and maintains the shape entangled with the stirrer 14. Thus, for most brands of coal, as illustrated in FIG. 1, the height a of the semicoke 16 adhering to the stirrer 14 from the bottom surface of the container 12 is the highest, and the height b of the semicoke 16 in contact with the inner wall of the container 12 from the bottom surface is the lowest. Such behavior of a thermally plasticized coal is known as the Weissenberg effect.

The heights, a and b, can be measured by disassembling the container 12 after measurement. After the measurement of the Gieseler fluidity, the container 12 may be scanned with a microfocus X-ray CT apparatus to capture an image of the shape of the semicoke 16, and the heights, a and b, may be measured from the image. The microfocus X-ray CT apparatus is, for example, XTH320LC manufactured by Nikon Corporation or phoenix v|tome|x m300 manufactured by GE Sensing & Inspection Technologies. The heights, a and b, vary little in the circumferential direction of the container, and it is therefore only necessary to measure the height in a specific cross section. If there is a difference in height depending on the position in the circumferential direction, the height may be measured in a plurality of cross sections, and the average value of the heights may be used as the height, a or b.

The shape of the semicoke 16 after the measurement of the Gieseler fluidity depends on the properties of coal. The inventors have examined the relationship between the degree of entanglement, $(a-b)/a$, represented by the heights, a and b, of the semicoke 16 and the coke strength considering that the relationship can indicate the effects of the shape of the semicoke 16 in the container 12 on the coke strength, and have confirmed that the degree of entanglement, $(a-b)/a$, is an index to determine whether the coal can reduce the coke strength. The inventors have also confirmed that, instead of the degree of entanglement, even the height, a, of the semicoke 16 adhering to the stirrer 14 can be an index to determine whether the coal can reduce the coke strength in the same manner as the degree of entanglement.

The relationship between the degree of entanglement, $(a-b)/a$, or the height, a, and the coke strength was examined as described below. To examine the effects of the degree of entanglement, $(a-b)/a$, and the height, a, on the coke strength, coals T to Y were subjected to a carbonization test. Table 1 shows the properties of the coals used. In the "Ash" and "Volatile matter" in Table 1 are values measured by proximate analysis according to JIS M 8812 (% by mass on a dry basis). "Ro" denotes the mean maximum vitrinite reflectance of coal according to JIS M 8816, and "TI" denotes the total inert (% by volume) in the analysis of coal macerals calculated using the Parr equation described in a method for measuring coal macerals according to JIS M 8816 and its explanation. "Log MF" denotes the common logarithm log of the maximum fluidity MF measured by a fluidity measurement method using the Gieseler plastometer method specified in JIS M 8801. As shown in Table 1, the coals T to Y have different properties.

The "Degree of entanglement" in Table 1 is the degree of entanglement, $(a-b)/a$, calculated from the heights, a and b, measured by the coal evaluation method according to the present embodiment using the Gieseler Plastometer illustrated in FIG. 1. The heights, a and b, were actually measured from an image of a cross-sectional shape of semicoke acquired by scanning the container 12 with the X-ray CT apparatus XTH320LC manufactured by Nikon Corporation.

It should be noted in Table 1 that the coals T and U have a height a of 30 mm or more and a degree of entanglement of 0.20 or more. In view of the properties of Ro and log MF in Table 1, the coal Y can be regarded as a standard coal in the technical field of producing metallurgical coke from coal.

In the present example, furthermore, coke was produced by carbonizing a coal mixture composed of two coals prepared by mixing each of the coals T to X with the coal Y at a ratio of 2:8. Table 2 shows the strength of the produced coke.

TABLE 2

| Item | Coke strength [DI 150/15] |
|------|---------------------------|
| Coal mixture TY | 84.0 |
| Coal mixture UY | 83.6 |
| Coal mixture VY | 84.6 |
| Coal mixture WY | 84.3 |
| Coal mixture XY | 84.7 |

A drum tester charged with a predetermined amount of coke was rotated 150 times at 15 rpm by a drum strength test method according to JIS K 2151. The mass fraction of coke with a grain size of 15 mm or more was measured. The drum index "DI 150/15", which is the ratio of the mass after the rotation to the mass before the rotation×100, was determined as coke strength. Table 2 lists the strength of coke produced from a coal mixture composed of two coals.

As shown in Table 2, the coke produced from the coal mixture of the coal T or U and the coal Y has lower coke strength than the coal mixture of the coal V, W, or X and the coal Y. The coals T and U have a degree of entanglement, (a−b)/a, of 0.20 or more or a height, a, of 30 mm or more. This shows that a coal with a degree of entanglement, (a−b)/a, of 0.20 or more is a poor raw coal for coke production. This also shows that a coal with a height, a, of 30 mm or more is a poor raw coal for coke production.

The range of the degree of entanglement, (a−b)/a, or the height, a, of a poor raw coal for coke production can be determined by examining the relationship between the degree of entanglement, (a−b)/a, or the height, a, and the strength of coke produced by mixing a plurality of coals having different degrees of entanglement, (a−b)/a, or different heights a with another coal and by carbonizing the coal mixture. In the present example, the coals T to X to be examined were added to the coal Y such that the amount of the coals T to X was constant, and were carbonized under the same conditions to produce coke. The carbonization test method for examining coal is not limited to this method and may be performed by fixing the addition amount of coal to be examined and adjusting the type or mixing amount of the other coal to make the average quality of the coal mixture containing the coal to be examined uniform. In such a case, the average quality to be made uniform is preferably the weighted average reflectance Ro or the weighted average log MF (a common logarithm of Gieseler maximum fluidity).

On the basis of the relationship between the coke strength and the degree of entanglement (a−b)/a or the height a, the range of the degree of entanglement, (a−b)/a, or the height, a, of a poor raw coal for coke production can be determined by the following method, for example. A blast furnace cannot be stably operated if low-strength coke is used. Thus, the coke strength for stable blast furnace operation is determined from the operation results of the blast furnace and the like, and the range of the degree of entanglement, (a−b)/a, or the height, a, corresponding to the coke strength for stable blast furnace operation is determined from the relationship between the coke strength and the degree of entanglement, (a−b)/a, or the height, a. A degree of entanglement, (a−b)/a, or a height, a, equal to or lower than the value thus determined results in stable blast furnace operation. However, a degree of entanglement, (a−b)/a, or a height, a, above this value is likely to result in unstable blast furnace operation. Thus, the range of the degree of entanglement, (a−b)/a, or the height, a, above the value can be the range of the degree of entanglement, (a−b)/a, or the height, a, of a poor raw material for coke production.

Although the properties of a coal rated as poor as a raw material for coke are determined from the strength test specified in JIS, another strength indicator may also be used. A known drum strength test method similar to the JIS method may be Micum strength, Tumbler strength, I-type drum index, or the like, which can be determined in accordance with ISO or ASTM standards. Furthermore, the range of the degree of entanglement or the height of a coke raw material rated as poor can be determined from the mechanical strength, such as compressive strength, of coke.

It is assumed that a coal with a high degree of entanglement or a coal with a large height, a, of the semicoke 16 adhering to the stirrer 14 has excessively high dilatability in its plastic state, easily forms a defect structure in coke after heating, and adversely affects the coke strength. Thus, in the present embodiment, a coal with a degree of entanglement or a height, a, equal to or higher than a predetermined value is regarded as a defective coal that can reduce the coke strength. More specifically, a coal satisfying at least one of a degree of entanglement of 0.20 or more and a height, a, of 30 mm or more under the measurement conditions for the fluidity of coal by the Gieseler plastometer method specified in JIS or the like is regarded as a defective coal for metallurgical coke. It can be judged that a higher degree of entanglement and a larger height a result in excessively high dilatability and more adversely affect the coke strength. Thus, it is not necessary to set the upper limit of the degree of entanglement and the height a. However, measured values of the degree of entanglement and the height a are limited by the size of the container 12 for a coal sample. Thus, the measurement is preferably performed using a container with which a degree of entanglement of 0.20 or more and a height a of 30 mm or more can be measured.

Depending on the brand of coal, the semicoke 16 may be entirely pulled by the stirrer 14 and may not be in contact with the inner wall of the container 12. Even in such a case, it is assumed that coal has excessively high dilatability. Thus, the degree of entanglement can be calculated to examine coal without problems and may be calculated to be 1 by substituting 0 for b.

When a coal rated as poor is used as a raw coal (coking coal) for coke, a coarse defect remains after coking, and a microstructure with a thin pore wall is formed. Thus, coke thus produced has lower coke strength. However, the inventors have found that even when a coal rated as poor is used as a raw coal for coke, the grain size of the coal rated as poor can be adjusted to reduce the decrease in strength.

Figure 2:
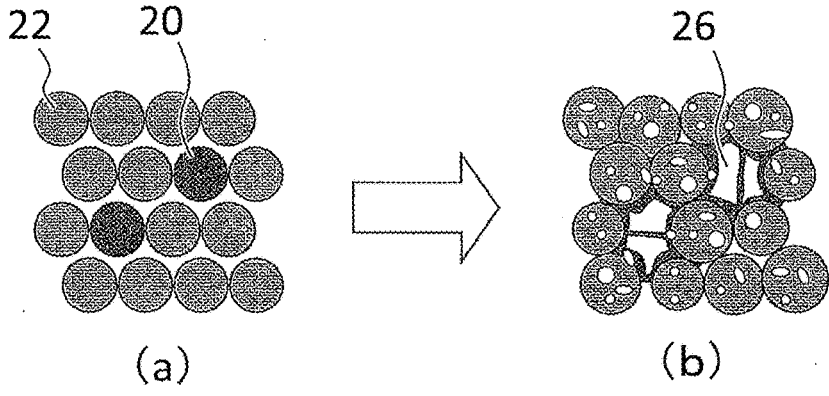
FIG. 2 is a schematic view of the formation state of a defect structure when a coal blend of coal grains 20 rated as poor and coal grains 22 not rated as poor is coked.

FIG. 2 is a schematic view of the formation state of a defect structure when a coal blend of coal grains 20 rated as poor and coal grains 22 not rated as poor is coked. FIG. 2(a) illustrates the state before the coking, and FIG. 2(b) illustrates the state after the coking. A coal grain 20 rated as poor swells and permeates deeply into a void between filled grains or into a coarse defect 26 during coking. Thus, a thin pore wall is formed, and a coarse defect 26 is formed in the original place of the coal grain 20. Due to the formation of the thin pore wall and the coarse defect 26, coke produced from a coal blend containing the coal grains 20 rated as poor has lower coke strength. Such a coarse defect 26 is formed even when only a coal rated as poor is carbonized (without blending with another coal). This is because the entire layer of a coal rated as poor swells, and this phenomenon causes a defect and reduces the coke strength. The inventors have found a correlation between the ease of formation of such a defect and the degree of entanglement, (a−b)/a, or the height, a.

Figure 3:
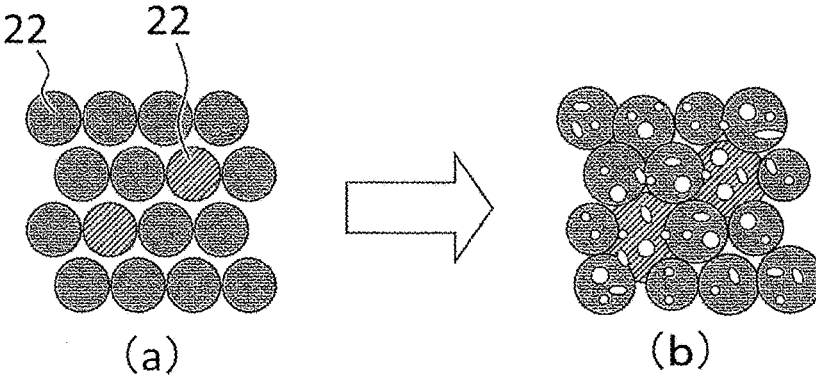
FIG. 3 is a schematic view of the formation state of a defect structure when a coal blend containing only coal grains 22 not rated as poor is coked.

FIG. 3 is a schematic view of the formation state of a defect structure when a coal blend containing only coal grains 22 not rated as poor is coked. FIG. 3(a) illustrates the state before the coking, and FIG. 3(b) illustrates the state after the coking. A coal grain 22 not rated as poor does not permeate deeply into a void between filled grains or into a coarse defect during coking. Thus, a thick pore wall is formed, and a coarse defect does not remain in the original place of the coal grain 22. Thus, coke produced from the coal grains 22 not rated as poor alone does not have a decrease in coke strength.

Figure 4:
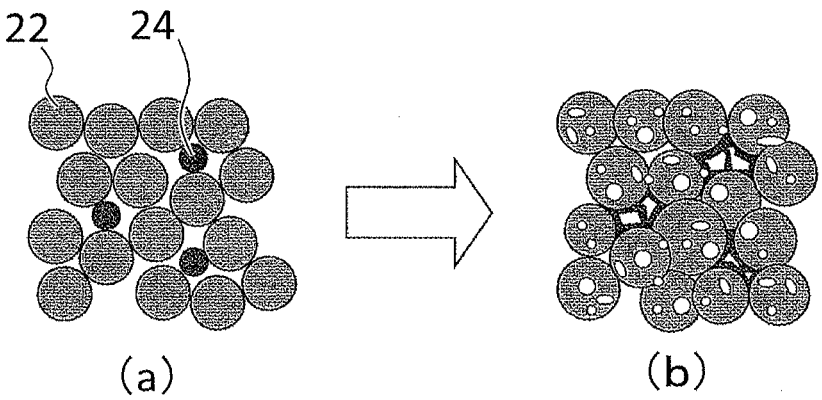
FIG. 4 is a schematic view of the formation state of a defect structure when a coal blend of finer coal grains 24, which are formed by pulverizing the coal grains 20 rated as poor, and the coal grains 22 not rated as poor is coked.

FIG. 4 is a schematic view of the formation state of a defect structure when a coal blend of finer coal grains 24, which are formed by pulverizing the coal grains 20 rated as poor, and the coal grains 22 not rated as poor is coked. FIG. 4(a) illustrates the state before the coking, and FIG. 4(b) illustrates the state after the coking. A coal rated as poor permeates deeply into a void between filled grains or into a coarse defect during coking. However, a defect formed in the original place of the grain becomes smaller. Thus, even when a coal blend containing a coal rated as poor is used, the use of the finer coal grains 24 formed by pulverizing the coal reduces the decrease in the coke strength of coke produced.

Thus, even using a coal rated as poor, pulverizing the coal in advance can reduce the occurrence of a coarse defect during coking. This reduces the decrease in the coke strength of coke after carbonization even using a coal rated as poor.

A caking additive added to a coal blend may also reduce the coke strength by the same mechanism. Thus, before a caking additive is delivered to a coke plant, the grain size of the caking additive is preferably adjusted to the grain size of a coal rated as poor.

To reduce the decrease in coke strength, the degree of pulverization of a coal rated as poor before blending and carbonization was examined. It was confirmed that the decrease in coke strength could be reduced by decreasing the amount of grains of 6 mm or more to 5% or less by mass in the coal before carbonization, that is, in the coal charged into a coke oven. As described in detail later, when the amount of grains of 6 mm or more in coal is 5% or less by mass, the coke strength of coke produced from a coal blend containing 8% or more by mass and less than 12% by mass of a coal rated as poor is the same as the coke strength of coke produced from a coal blend containing 2% or less by mass of a coal rated as poor. This result means that when the amount of grains of 6 mm or more in coal is 5% or less by mass, the coke strength does not change even if the blending ratio of a coal rated as poor is 8% or more by mass and less than 12% by mass or 2% or less by mass. This can reduce the decrease in the coke strength due to blending of a coal rated as poor.

Coke is typically produced from a coal blend of 10 to 15 brands of coal. A coal or a caking additive delivered to a coke plant is further pulverized into fine grains suitable for coke production. In a coke plant for producing coke, however, adjusting only a specific brand of coal to a specific grain size makes the operation complicated and is undesirable. Thus, the grain size of a coal rated as poor is preferably adjusted in advance before the coal is delivered to a coke-making plant. This allows the coal to be further pulverized in a pulverization process before charged into a coke oven. This eliminates the need to adjust the grain size in a coke-making plant, which requires complicated operations, and can reduce the decrease in the coke strength of coke produced.

The amount of grains of 6 mm or more in coal can be calculated from the mass ratio of grains above or below a sieve to the total sample by drying the coal to a moisture content of 6% or less by mass and passing the coal through a sieve with a predetermined mesh size. When the moisture content of coal is 6% or less by mass, grains of the coal do not aggregate and form pseudo-grains, or a fine powder does not adhere to coarse grains. Thus, the measured grain size has no error. Thus, the amount of grains with a grain size of 6 mm or more in coal is preferably measured when the coal has a moisture content of 6% or less by mass.

A coal delivered to a coke plant is further pulverized in the coke plant and is then charged into a coke oven. Thus, the amount of grains with a grain size of 6 mm or more in coal before the coal is delivered to a coke plant is not necessarily 5% or less by mass. Thus, the grain size of coal was determined when the amount of grains with a grain size of 6 mm or more in the coal was 5% or less by mass after the coal was pulverized under the pulverization conditions in a typical coke plant. As a result, it was found that when the amount of grains with a grain size of 6 mm or more in coal was 30% or less by mass, the amount of grains with a grain size of 6 mm or more was 5% or less by mass after the coal was pulverized under typical coal pulverization conditions. Thus, the grain size of a coal rated as poor may be adjusted such that the amount of grains with a grain size of 6 mm or more in the coal before the coal is delivered to a coke plant is 30% or less by mass, and the amount of grains with a grain size of 6 mm or more in the coal before the coal is charged into a coke oven is adjusted to 5% or less by mass by pulverization in the coke plant.

To decrease the grain size of coal, for example, the grain size of the coal may be adjusted by a mining method that can decrease the grain size in a coal mining step or by pulverization, classification, or sieving in a coal preparation process or in a blending process after mining and before delivery. In a coal mine, the quality of coal produced from each coal seam is measured in advance. Thus, the degree of entanglement may also be measured, and the grain size may be adjusted on the basis of the measured value. Coal may be pulverized with a known crusher, such as an impact crusher or a hammer crusher. Furthermore, such a crusher can be used in combination with a sieve to taken out and pulverize only a coarse grain portion of the coal responsible for lower coke strength and to more effectively adjust the grain size. It should be noted that the grain size of coal inevitably varies depending on various conditions, such as the place and time of mining, equipment, transportation after mining, and storage, and therefore varies from lot to lot. Thus, the grain size of coal may be adjusted by blending lots with different grain sizes.

The grain size of coal may also be adjusted in consideration of the hardness of the coal. Softer coal is pulverized more finely under the same pulverization conditions. When the target value of the amount of grains with a grain size of 6 mm or more after pulverization in a coke plant is constant at 5% or less by mass, soft coal can satisfy a predetermined target value even if the amount of grains with a grain size of 6 mm or more is large before the soft coal is supplied to a crusher in a coke plant. A Hardgrove grindability index (HGI) is generally used as an index of the hardness of coal. When the amount of grains with a grain size of 6 mm or more in coal was 30% by mass and when the amount of grains with a grain size of 6 mm or more in the coal after the coal was pulverized under typical coal pulverization conditions was 5% or less by mass, the coal had a HGI of 60. The HGI is an index determined by a pulverization test method described in JIS M 8801.

A coal with a higher HGI is softer. It was found that the amount of grains with a grain size of 6 mm or more in pulverized coal could be decreased to 5% or less by mass even if the amount of grains with a grain size of 6 mm or more before the coal was supplied to a crusher in a coke plant was increased by 0.5% by mass for each increase in the HGI (softening) of the coal by 1. This finding shows that the grain size is preferably adjusted such that the amount of grains with a grain size of 6 mm or more before a coal rated as poor is delivered to a coke plant or before the coal is delivered from a coal production site satisfies the following formula (1):

$$\text{Amount of grains with a grain size of 6 mm or more}$$
$$(\% \text{ by mass}) \leq 30 + 0.5 \times (\text{HGI} - 60) \qquad (1)$$

Although the HGI of coal typically ranges from 40 to 100, the HGI of a coal rated as poor was measured to be in the range of approximately 60 to 80. Thus, it can be said that a coal with a HGI of 60 is the hardest coal rated as poor, and at least when the amount of grains with a grain size of 6 mm or more in a coal rated as poor is 30% or less by mass, the amount of grains with a grain size of 6 mm or more in the coal after the coal is pulverized under typical coal pulverization conditions in a coke plant is 5% or less by mass. In consideration of variations in the HGI of coal, the amount of grains with a grain size of 6 mm or more in a coal rated as poor is preferably 20% or less by mass.

A coal in which the grain size is adjusted by a method for preparing a coal or a caking additive according to the present embodiment is an individual brand of coking coal and is defined as a unit of coking coal that is managed as a single lot at the point in time when the coal is delivered to a coke-making plant or delivered from a coal production site. The phrase "managed as a single lot", as used herein, includes cases where the properties of the whole lot are represented by a representative analytical value obtained by sampling from the lot, cases where the whole lot is loaded present embodiment, an individual brand of coal from a mine or a shipping base may be delivered by any means (a ship, a freight car, etc.) in any step (for delivery by a freight car and then by a ship, both of them correspond delivery). This is because the composition and grain size of coal once recognized as an individual brand of coal do not change thereafter except for incidental ones.

Example 1

A method for determining the optimum grain size of a coal rated as poor is described below. First, the effects of the difference in the shape of semicoke after heating and stirring on the coke strength were examined. The shape of semicoke after Gieseler fluidity measurement was measured in 18 coals (coals A to R) and one caking additive (a caking additive S). Table 3 shows the properties of the coals and the caking additive used. In Table 3, Ro denotes the mean maximum vitrinite reflectance of coal according to JIS M 8816, and log MF is a common logarithm of maximum fluidity (MF) measured by the Gieseler plastometer method. Volatile matter (VM) and ash (Ash) are measured by the proximate analysis according to JIS M 8812.

TABLE 3

| Coal | Ro [%] | log MF [log ddpm] | VM [mass %] | Ash [mass %] | Degree of entanglement [-] | Height, a [mm] |
|---|---|---|---|---|---|---|
| Coal A | 0.66 | 3.55 | 43.2 | 5.8 | 0.17 | 28 |
| Coal B | 0.67 | 1.00 | 36.6 | 9.0 | 0.00 | 24 |
| Coal C | 0.72 | 3.61 | 40.8 | 9.0 | 0.23 | 30 |
| Coal D | 0.73 | 2.29 | 36.2 | 8.8 | 0.01 | 25 |
| Coal E | 0.75 | 2.32 | 38.1 | 9.7 | 0.05 | 25 |
| Coal F | 0.80 | 3.17 | 37.2 | 7.9 | 0.24 | 31 |
| Coal G | 0.91 | 3.59 | 33.0 | 7.9 | 0.34 | 33 |
| Coal H | 1.02 | 2.48 | 29.1 | 8.6 | 0.04 | 27 |
| Coal I | 1.00 | 1.71 | 25.8 | 9.6 | 0.00 | 23 |
| Coal J | 1.00 | 2.20 | 27.7 | 10.4 | 0.00 | 24 |
| Coal K | 1.03 | 2.97 | 28.2 | 9.6 | 0.16 | 27 |
| Coal L | 1.14 | 1.77 | 24.2 | 9.2 | 0.00 | 24 |
| Coal M | 1.30 | 1.34 | 21.0 | 9.4 | 0.00 | 23 |
| Coal N | 1.31 | 1.26 | 20.4 | 7.3 | 0.00 | 22 |
| Coal O | 1.38 | 2.49 | 20.9 | 10.9 | 0.11 | 27 |
| Coal P | 1.44 | 2.03 | 21.1 | 9.3 | 0.00 | 26 |
| Coal Q | 1.54 | 0.00 | 16.6 | 8.3 | 0.00 | 23 |
| Coal R | 1.62 | 0.70 | 18.8 | 9.6 | 0.00 | 24 |
| Caking additive S | — | 4.8 or more | — | less than 1 | 1.00 | 35 | in a coal yard as a single lot, cases where the whole lot is put in the same coal tank, and cases where the whole lot is traded as a single lot or as a single brand name in a purchase contract. Thus, in the present embodiment, when the grain size of coal is adjusted before the coal is delivered to a coke-making plant, the coal is defined as a single brand of coking coal.

The phrase "delivered to a coke plant", as used herein, refers to delivery to a coal yard or a coal hopper attached to the coke plant for pulverization to a grain size suitable for coke production in the coke plant or for blending with another brand of coal. For example, in a steelworks in a waterfront district, coal is delivered to a raw material wharf and then to a coal yard attached to a coke plant. In this case, the delivery to the raw material wharf is regarded as the delivery to the coke plant.

The phrase "delivered from a coal production site", as used herein, refers to delivery of an individual brand of coal from a mine or a shipping base by means of transportation, such as a ship, a freight car, a truck, or a conveyor. In the Using the Gieseler plastometer 10 illustrated in FIG. 1, the heights, a and b, were measured from the shape of semicoke formed after heating and stirring, and the degree of entanglement, (a−b)/a, was calculated. The values in the column of "Degree of entanglement" in Table 3 are values of the degree of entanglement, (a−b)/a, and the values in the column of "Height, a" are values of the height, a, of semicoke adhering to the stirrer. The heights, a and b, of the semicoke were measured on an image of the semicoke 16 acquired by scanning the container 12 with an XTH320LC manufactured by Nikon Corporation after heating and stirring.

The coals C, F, and G of the coals shown in Table 3 had a degree of entanglement, (a−b)/a, of 0.20 or more. Thus, the coals C, F, and G were regarded as defective coals that may reduce the coke strength. Table 3 shows that whether the coal is defective coal can be judged by whether the height, a, is 30 mm or more.

In a known coal blending theory for estimating coke strength, it has been thought that the coke strength is mainly determined by the mean maximum vitrinite reflectance (Ro) and log MF of coal (see Non-patent Literature 1, for example). Thus, a coal blend of various coals was produced such that the weighted average, Ro, and the weighted average, log MF, of the whole coal blend were the same (Ro=0.99, log MF=2.2). The coal A and the coal F were prepared by pulverizing the coal such that the amount of grains with a grain size of less than 1 mm was 100% by mass, the amount of grains with a grain size of less than 3 mm was 100% by mass, or the amount of grains with a grain size of less than 6 mm was 100% by mass. The other coals were pulverized such that the amount of grains with a grain size of less than 3 mm was 100 by mass. These coals were used to prepare six levels of coal blends (A1 to A3 and F1 to F3). Table 4 shows the blending ratios of these coal blends. [%] of the blending ratios in Table 4 indicates by mass.

Figure 5:
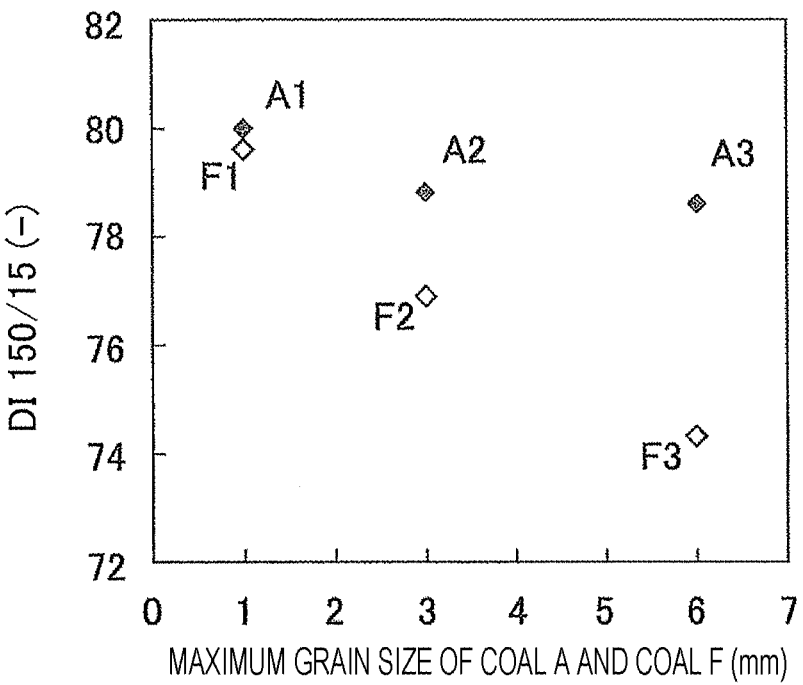
FIG. 5 is a graph of the relationship between the maximum grain size of coal A and coal F and the drum index.

FIG. 5 is a graph of the relationship between the maximum grain size of the coals A and F and the drum index. The coke produced from the coal blend containing the coal F rated as poor had lower strength at all grain sizes than the coke produced from the coal blend containing the coal A not rated as poor. Although the experiment was conducted under the conditions that the values of Ro and log MF of the coals A and F were not significantly different and that the weighted averages of Ro and log MF of the coal blends were the same, there was a difference in coke strength. Thus, the degree of entanglement and the height a measured in the present embodiment are factors that have an influence on the coke strength and that cannot be explained by the conventionally used Ro or log MF.

The test results show that the addition of the coal A with a degree of entanglement of 0.17 and a height a of 28 mm to the coal blend is less likely to reduce the coke strength,

TABLE 4

| | Blending ratio | | | | | |
| Coal | Coal blend A1 [%] | Coal blend A2 [%] | Coal blend A3 [%] | Coal blend F1 [%] | Coal blend F2 [%] | Coal blend F3 [%] |
|---|---|---|---|---|---|---|
| Coal A | 20 | 20 | 20 | 0 | 0 | 0 |
| Coal B | 14 | 14 | 14 | 13 | 13 | 13 |
| Coal F | 0 | 0 | 0 | 20 | 20 | 20 |
| Coal H | 19 | 19 | 19 | 20 | 20 | 20 |
| Coal J | 13 | 13 | 13 | 20 | 20 | 20 |
| Coal L | 11 | 11 | 11 | 11 | 11 | 11 |
| Coal N | 11 | 11 | 11 | 7 | 7 | 7 |
| Coal O | 8 | 8 | 8 | 9 | 9 | 9 |
| Coal R | 4 | 4 | 4 | 0 | 0 | 0 |
| Coal A, Coal F maximum grain size [mm] | 1 | 3 | 6 | 1 | 3 | 6 |
| Weighted average Ro [%] | 0.99 | 0.99 | 0.99 | 0.99 | 0.99 | 0.99 |
| Weighted average log MF [log ddpm] | 2.2 | 2.2 | 2.2 | 2.2 | 2.2 | 2.2 |
| DI 150/50 [-] | 80.0 | 78.8 | 78.5 | 79.6 | 76.9 | 74.3 |
| CSR [%] | 58.0 | 55.9 | 55.2 | 57.6 | 50.5 | 47.5 |
| MSI + 65 [%] | 53.0 | 51.8 | 51.5 | 52.4 | 49.5 | 46.7 |

The coal A has a degree of entanglement, (a−b)/a, of 0.17 and is not rated as poor. On the other hand, as described above, the coal F has a degree of entanglement, (a−b)/a, of 0.24 and is rated as poor.

The moisture content of the whole coal blend was adjusted to 8% by mass, and 16 kg of the coal blend was charged into a carbonization vessel at a bulk density of 750 kg/m³. A 10-kg weight was put on the coal blend, and the coal blend was carbonized in an electric furnace at a furnace wall temperature of 1050° C. for 6 hours. The carbonization vessel was then taken out from the electric furnace and was cooled with nitrogen. Thus, coke was produced. The mass fraction of coke with a grain size of 15 mm or more in the produced coke was measured by the drum strength test method according to JIS K 2151 after 150 revolutions at 15 rpm. The coke strength was calculated as the drum index DI 150/15, which was the ratio of the mass after the rotation to the mass before the rotation. Furthermore, the coal strength after hot $CO_2$ reaction according to the ISO 18894 method (CSR) and the micro strength index (MSI+65) were also measured. Table 4 also shows these measurement results.

but the addition of the coal F with a degree of entanglement of 0.24 and a height a of 31 mm to the coal blend tends to reduce the coke strength. Thus, it is appropriate to rate a coal that satisfies at least one of the degree of entanglement of 0.20 or more and the height a of 30 mm or more as poor as a coal for metallurgical coke production. To more reliably prevent the decrease in coke strength, the criterion for rating coal as poor may be tightened, and a coal that satisfies at least one of the degree of entanglement of more than 0.17 and the height a of more than 28 mm may be rated as poor as a coal for metallurgical coke production. Furthermore, in both the coal blend containing the coal A not rated as poor and the coal blend containing the coal F rated as poor, the coke strength of produced coke was improved by reducing the coal grain size. In particular, in the coal blend containing the coal F rated as poor, the coke strength was significantly improved by reducing the coal grain size.

Next, the degree of pulverization of a coal rated as poor was examined in an actual coke oven. In general, in the normal operation of an actual coke oven, individual brands of coal are mixed at a predetermined blending ratio and are then pulverized. The grain size of the coal blend is controlled by the mass fraction of grains above or below a sieve to the total mass when the coal blend is passed through a predetermined sieve mesh.

Each of two coal blends prepared by changing the amount of grains with a grain size of 6 mm or less in a coal rated as poor (a coal blend with a blending ratio of defective coal of 2% or less by mass and a coal blend with a blending ratio of defective coal of 8% or more by mass and less than 12% by mass) was carbonized in an actual coke oven, and the drum index DI 150/15 was determined as coke strength after the carbonization. Table 5 below shows the average properties of the coal blends used (the weighted averages of the characteristic values of each coal in each coal blend based on the blending ratio), the carbonization temperature (the temperature of a firing chamber), and the temperature in coal after carbonization (the temperature of coke at the center in the height direction and in the width direction of a carbonization chamber). The coal blends were prepared such that the range of variation in the average properties, the carbonization temperature, and the temperature in coal after carbonization was decreased to eliminate the effects of these factors on the coke strength. The relationship between the amount of grains with a grain size of 6 mm or more in the coal blends and the coke strength was examined from the measurement results, and the degree of pulverization of a coal rated as poor was examined. The conditions in Table 5 are examples of the conditions used in the test. In general, good coke can be produced when, in the average properties of the coal blends, Ro ranges from 0.9% to 1.3%, log MF ranges from 2.3 to 3.0, and the moisture content ranges from 3% to 12% by mass, and when the coke temperature after carbonization ranges from 900° C. to 1200° C.

TABLE 5

| | | |
|---|---|---|
| Coal blend | Ro [%] | 0.98-1.02 |
| average | log MF [log ddpm] | 2.6-2.8 |
| properties | Moisture content [mass %] | 8.5-10.5 |
| Carbonization | Carbonization temperature [° C.] | 1090-1105 |
| conditions | Temperature in coal after carbonization [° C.] | 990-1115 |

Figure 6:
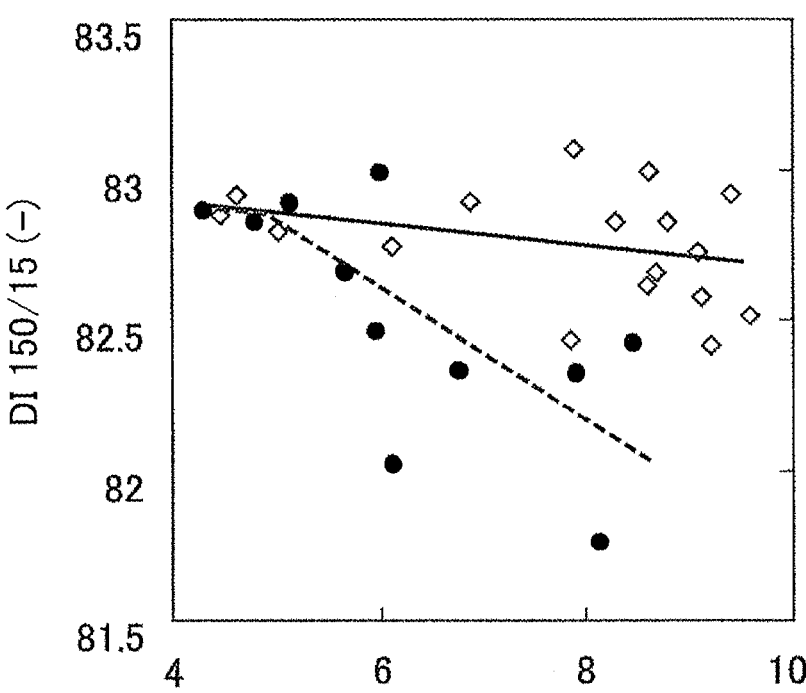
FIG. 6 is a graph of the relationship between the amount of grains with a grain size of 6 mm or more in a coal blend and the coke strength.

FIG. 6 is a graph of the relationship between the amount of grains with a grain size of 6 mm or more in the coal blends and the coke strength. As illustrated in FIG. 6, when the blending ratio of a coal rated as poor was relatively high in the range of 8% or more by mass and less than 12% by mass, the amount of grains with a grain size of 6 mm or more increased, and the coke strength of coke produced decreased greatly when the whole coal grain size increased. In contrast, the coal blends containing 2% or less by mass of a coal rated as poor had a smaller decrease in the coke strength due to coarse coal grains. This indicates that even in a coal blend with the same grain size as a whole, when the coal blend contains a coal rated as poor, the coke strength of coke produced from the coal blend decreases.

On the other hand, when the amount of grains of 6 mm or more in the coal blend is approximately 5% or less by mass, even if the coal blend contains 8% or more by mass and less than 12% by mass of a coal rated as poor, coke produced had almost the same strength as coke produced without the coal rated as poor (2% or less by mass). It is inferred from this result that pulverization that decreases the amount of grains of 6 mm or more to 5% or less by mass can reduce the decrease in the coke strength due to the blend of a coal rated as poor. A coal with a large degree of entanglement tends to have a coarse defect as illustrated in FIG. 2. Thus, it is thought that the amount of coal grains with a large grain size could be decreased to reduce the formation of a coarse defect and significantly reduce the decrease in the coke strength.

Next, the effect of improving coke strength by adjusting the grain size of an individual brand is described below. In a production area of the coal G shown in Table 3, although the amount of grains of 6 mm or more in the coal G delivered after ordinary mining and coal preparation was 39% by mass, the coal G after the coal preparation was pulverized with an impact crusher to adjust the grain size such that the amount of grains of 6 mm or more in the coal G was 30% by mass. This coal is referred to as coal G'. After the coals G and G' were delivered to a coke plant, the coal G or G' was blended with the coals A, B, H, J, L, N, O, and R such that the blending ratio of the coal G or G' is 10% by mass. Thus, a coal blend with a weighted average reflectance of 1.01% and a weighted average log MF of 2.4 was prepared. The degree of entanglement of the coals G and G' was measured by the method described with respect to Table 1. The degree of entanglement of the coals G and G' was 0.34. Thus, the coal G was rated as poor.

Each of a coal blend g containing the coal G and a coal blend g' containing the coal G' was pulverized with an impact crusher in a coke plant such that the amount of grains of 3 mm or less was 78% by mass. The amount of grains of 6 mm or more in the coal blend g or g' after the pulverization was 5.5% by mass. The coal blend was carbonized in a coke oven at an operating rate of 125%, and the produced coke was dry quenched. The JIS drum index DI 150/15 was then measured. As a result, the coke produced from the coal blend g had a drum index of 82.9, whereas the coke produced from the coal blend g' had a drum strength of 83.1. These results show that adjusting the amount of grains of 6 mm or more to 30% by mass in the individual brand of coal before the coal is delivered to the coke plant can reduce the decrease in the coke strength of coke produced even using a coal rated as poor, and high-strength metallurgical coke can be produced.

The test was conducted using the coal K (the amount of grains of 6 mm or more at the time of delivery from the production area was 37% by mass) instead of the coal G. As a result, the coke strength was 83.0 in both the case where the grain size was adjusted such that the amount of grains of 6 mm or more in the coal K was 30% by mass and the case where the grain size was not adjusted. Thus, adjusting the grain size of coal did not have the effect of improving the coke strength. In the coal K, the semicoke has a degree of entanglement of 0.16, which is less than 0.20, and the semicoke adhering to the stirrer has a height of 27 mm, which is less than 30 mm. Thus, the coal K is a coal not rated as poor, and the coke strength of coke produced is not improved even if the grain size of such a coal is adjusted in advance. This result shows that, in the method for preparing a coal or a caking additive according to the present embodiment, determining whether the coal is rated as poor or not and adjusting the grain size of a coal rated as poor can reduce the decrease in the coke strength of coke produced and realize the production of high-strength metallurgical coke. Furthermore, determining whether the coal is rated as poor or not, selecting a coal rated as poor, and adjusting the grain size of the coal rated as poor can decrease the amount of coal to be subjected to the grain size adjustment, which contributes to a reduction in load required for coke production and to energy conservation.

The invention claimed is:

1. A method for preparing a coal, or a caking additive as a raw material for coke production, the method comprising:

before the coal or the caking additive is delivered to a coke plant, adjusting a grain size of the coal or caking additive such that a portion of grains with a grain size of 6 mm or more in the coal or the caking additive has at least one of (i) a degree of entanglement (a−b)/a of 0.20 or more, and (ii) a portion having a height a of 30 mm or more is 30% or less by mass, heating and stirring the coal or caking additive in a container to form a semicoke, wherein the height a is a height of the semicoke adhering to a stirrer, and a height b is a height of the semicoke on an inner wall of the container.

2. A method for preparing a coal or a caking additive as a raw material for coke production, the method comprising:

before the coal or the caking additive is delivered to a coke plant, adjusting a grain size of the coal or caking additive such that a portion of grains with a grain size of 6 mm or more in the coal or caking additive has at least one of (i) a degree of entanglement (a−b)/a of 0.20 or more, and (ii) a portion having a height a of 30 mm or more, which satisfies a formula (1):

$$\text{amount of grains with a grain size of 6 mm or more} \atop \text{(\% by mass)} \leq 30 + 0.5 \times (\text{HGI} - 60) \qquad (1)$$

wherein HGI denotes a Hardgrove grindability index of the coal or the caking additive in accordance with JIS M8801, and heating and stirring the coal or caking additive in a container to form a semicoke, wherein the height a is a height of a semicoke adhering to a stirrer, and a height b is a height of the semicoke on an inner wall of the container.

3. The method for preparing a coal or a caking additive according to claim 1, wherein the container and the stirrer are a Gieseler plastometer.

4. The method for preparing a coal or a caking additive according to claim 1, further comprising, before the coal or the caking additive is charged into a coke oven, adjusting the grain size such that the amount of grains with a grain size of 6 mm or more in the coal or the caking additive is 5% or less by mass.

5. The method for preparing a coal or a caking additive according to claim 1, further comprising, before the coal or the caking additive is delivered from a place where the coal or the caking additive is produced, adjusting the grain size of the coal or the caking additive.

6. A method for producing coke, the method comprising carbonizing a coal prepared by the method for preparing a coal or a caking additive according to claim 1.

7. A method for producing coke, the method comprising carbonizing a coal and a caking additive prepared by the method for preparing a coal or a caking additive according to claim 1.

8. The method for preparing a coal or a caking additive according to claim 2, wherein the container and the stirrer are a Gieseler plastometer.

9. The method for preparing a coal or a caking additive according to claim 2, further comprising, before the coal or the caking additive is charged into a coke oven, adjusting the grain size such that a portion of grains with a grain size of 6 mm or more in the coal or the caking additive is 5% or less by mass.

10. The method for preparing a coal or a caking additive according to claim 2, further comprising, before the coal or the caking additive is delivered from a place where the coal or the caking additive is produced, adjusting the grain size of the coal or the caking additive.

* * * * *